US011116925B2

(12) United States Patent
Sinderby et al.

(10) Patent No.: US 11,116,925 B2
(45) Date of Patent: Sep. 14, 2021

(54) DEVICE, METHOD AND SYSTEM FOR PROVIDING VENTILATORY ASSIST TO A PATIENT

(71) Applicant: UNITY HEALTH TORONTO, Toronto (CA)

(72) Inventors: Christer Sinderby, Toronto (CA); Jennifer Beck, Toronto (CA); Norman Comtois, Scarborough (CA)

(73) Assignee: UNITY HEALTH TORONTO, Toronto (CA)

( * ) Notice: Subject to any disclaimer, the term of this patent is extended or adjusted under 35 U.S.C. 154(b) by 687 days.

(21) Appl. No.: 15/193,696

(22) Filed: Jun. 27, 2016

(65) Prior Publication Data
US 2016/0303340 A1  Oct. 20, 2016

Related U.S. Application Data

(63) Continuation-in-part of application No. PCT/CA2014/051260, filed on Dec. 23, 2014.
(Continued)

(51) Int. Cl.
*A61M 16/04* (2006.01)
*A61M 16/16* (2006.01)
(Continued)

(52) U.S. Cl.
CPC ...... *A61M 16/0486* (2014.02); *A61M 16/024* (2017.08); *A61M 16/04* (2013.01);
(Continued)

(58) Field of Classification Search
CPC ............ A61M 16/0486; A61M 16/161; A61M 16/204; A61M 16/205; A61M 16/024;
(Continued)

(56) References Cited

U.S. PATENT DOCUMENTS 4,340,044 A * 7/1982 Levy ................... A61M 16/024
128/204.21
4,596,247 A * 6/1986 Whitwam ........... A61M 16/127
128/204.25
(Continued)

FOREIGN PATENT DOCUMENTS

| WO | 0124861 | 4/2001 | |
|---|---|---|---|
| WO | WO-0124861 A1 * | 4/2001 | ............ A61M 16/04 |
| WO | 2012000096 | 1/2012 | |

*Primary Examiner* — Jan Christopher L Merene
*Assistant Examiner* — Brian T Khong
(74) *Attorney, Agent, or Firm* — Fay Kaplun & Marcin, LLP

(57) ABSTRACT

A device for providing ventilatory assist to a patient has a manifold having an inspiratory port to receive an inspiratory flow from an inspiratory supply line, an interface port connectable to an external end of an endotracheal tube inserted in a patient's trachea and an expiratory port configured to receive an expiratory flow from the endotracheal tube via the interface port. An inspiratory lumen has a distal end insertable in the endotracheal tube. A cross-section of the inspiratory lumen is smaller than that of the endotracheal tube to allow gas flowing in the endotracheal tube. The inspiratory flow is directed to the inspiratory lumen, or to the endotracheal tube, or at once to the inspiratory lumen and to the endotracheal tube.

31 Claims, 11 Drawing Sheets

Related U.S. Application Data

(60) Provisional application No. 61/921,142, filed on Dec. 27, 2013.

(51) Int. Cl.
*A61M 16/20* (2006.01)
*A61M 16/00* (2006.01)
*A61M 16/08* (2006.01)

(52) U.S. Cl.
CPC .......... *A61M 16/16* (2013.01); *A61M 16/161* (2014.02); *A61M 16/20* (2013.01); *A61M 16/204* (2014.02); *A61M 16/205* (2014.02); *A61M 16/08* (2013.01); *A61M 2016/0015* (2013.01); *A61M 2016/0021* (2013.01); *A61M 2016/0027* (2013.01); *A61M 2202/0208* (2013.01); *A61M 2230/005* (2013.01); *A61M 2230/08* (2013.01); *A61M 2230/202* (2013.01); *A61M 2230/432* (2013.01)

(58) Field of Classification Search
CPC ...... A61M 16/04; A61M 16/16; A61M 16/20; A61M 16/08; A61M 16/201; A61M 16/1015; A61M 16/0404; A61M 2016/0015; A61M 2016/0021; A61M 2016/0027; A61M 2016/0413; A61M 2016/0036; A61M 2202/0208; A61M 2230/005; A61M 2230/08; A61M 2230/202; A61M 2230/432; A61M 16/042; A61M 16/048; A61M 16/0422–0431; A61M 16/202–203
See application file for complete search history.

(56) References Cited

U.S. PATENT DOCUMENTS

| | | | | |
|---|---|---|---|---|
| 4,676,239 A | * | 6/1987 | Humphrey | A61M 16/08 128/203.28 |
| 5,092,326 A | * | 3/1992 | Winn | A61M 16/0096 128/205.13 |
| 5,303,698 A | * | 4/1994 | Tobia | A61M 16/024 128/204.21 |
| 5,311,861 A | * | 5/1994 | Miller | A61M 16/08 128/201.13 |
| 5,400,778 A | | 3/1995 | Jonson et al. | |
| 5,423,313 A | * | 6/1995 | Olsson | A61M 16/0051 128/204.21 |
| 5,555,880 A | * | 9/1996 | Winter | A61M 16/0096 128/204.21 |
| 5,664,562 A | * | 9/1997 | Bourdon | A61M 16/0069 128/204.18 |
| 5,671,752 A | | 9/1997 | Sinderby et al. | |
| 5,740,796 A | * | 4/1998 | Skog | A61B 5/08 128/204.18 |
| 5,752,506 A | * | 5/1998 | Richardson | A61M 16/0096 128/204.18 |
| 5,820,560 A | | 10/1998 | Sinderby et al. | |
| 5,896,854 A | * | 4/1999 | Bliss | A61M 16/024 128/200.24 |
| 6,196,222 B1 | * | 3/2001 | Heinonen | A61M 16/12 128/204.18 |
| 6,298,848 B1 | * | 10/2001 | Skog | A61M 15/0086 128/204.18 |
| 6,439,228 B1 | | 8/2002 | Hete et al. | |
| 6,588,423 B1 | | 7/2003 | Sinderby | |
| 6,609,521 B1 | * | 8/2003 | Belani | A61M 16/04 128/207.14 |
| 6,901,286 B1 | | 5/2005 | Sinderby et al. | |
| 7,661,427 B2 | | 2/2010 | Sinderby et al. | |
| 9,339,208 B2 | * | 5/2016 | Wood | A61B 5/08 |
| 2002/0104537 A1 | | 8/2002 | Banner | A61M 16/0012 128/204.25 |
| 2003/0066528 A1 | * | 4/2003 | Hill | A61M 16/026 128/204.18 |
| 2003/0168066 A1 | * | 9/2003 | Sallvin | A61M 16/00 128/204.21 |
| 2003/0183232 A1 | * | 10/2003 | Fukunaga | A61M 16/0081 128/204.18 |
| 2004/0003814 A1 | * | 1/2004 | Banner | A61M 16/042 128/204.21 |
| 2004/0221854 A1 | * | 11/2004 | Hete | A61M 16/042 128/207.16 |
| 2005/0085867 A1 | * | 4/2005 | Tehrani | A61N 1/3601 607/42 |
| 2007/0101992 A1 | * | 5/2007 | Soliman | A61M 16/0051 128/204.21 |
| 2007/0221224 A1 | * | 9/2007 | Pittman | A61M 16/0069 128/204.22 |
| 2008/0060646 A1 | * | 3/2008 | Isaza | A61M 16/0468 128/204.21 |
| 2008/0178880 A1 | * | 7/2008 | Christopher | A61M 16/0051 128/204.23 |
| 2008/0185006 A1 | * | 8/2008 | Harand | A61M 16/0833 128/207.16 |
| 2011/0178419 A1 | * | 7/2011 | Wood | A61M 16/0484 600/529 |
| 2012/0065533 A1 | * | 3/2012 | Carrillo, Jr. | A61B 5/083 600/532 |
| 2012/0167884 A1 | * | 7/2012 | Cardelius | A61B 5/091 128/204.21 |
| 2012/0298108 A1 | * | 11/2012 | Kane | A61M 16/0066 128/204.23 |
| 2013/0327332 A1 | * | 12/2013 | Nilsson | A61M 16/1015 128/205.24 |
| 2013/0340758 A1 | * | 12/2013 | Schindhelm | A61M 16/0051 128/204.23 |
| 2013/0345572 A1 | * | 12/2013 | Karbing | A61B 5/0205 600/484 |
| 2014/0190485 A1 | * | 7/2014 | Milne | A61M 16/0051 128/205.23 |
| 2014/0311491 A1 | * | 10/2014 | Klein | A61B 5/083 128/204.22 |
| 2015/0059753 A1 | * | 3/2015 | Hill | A61M 16/00 128/204.23 |
| 2016/0136368 A1 | * | 5/2016 | Spandorfer | A61M 16/14 128/201.13 |
| 2016/0235939 A1 | * | 8/2016 | Sardesai | A61M 16/209 |

* cited by examiner

DEVICE, METHOD AND SYSTEM FOR PROVIDING VENTILATORY ASSIST TO A PATIENT

This application is a continuation-in-part (CIP) bypass application of International Patent Application No. PCT/CA2014/051260 filed on Dec. 23, 2014, and which claims priority to U.S. Provisional Patent Application No. 61/921,142 filed on Dec. 27, 2013. The disclosures of both of the above-mentioned applications are incorporated herein in their entirety.

TECHNICAL FIELD

The present disclosure relates to the field of ventilatory assist systems. More specifically, the present disclosure relates to a device, a method and a system for providing ventilatory assist to a patient.

BACKGROUND

A recurring problem in patients with impaired function of the respiratory system is that the volume of air-exchanging lung parenchyma is reduced. This may be caused by either edema, lung collapse and/or other factors. When a volume of air-transporting parenchyma/airways comprising, for example, the main bronchi, trachea, and upper airways of the patient is maintained, the volume of air-exchanging lung parenchyma decreases relative to the volume of air-transporting parenchyma/airways. In situations of increased need for $CO_2$ removal, a ventilatory contribution may be hampered if a dead space, or dead volume, in air-transporting parenchyma/airways and in a respiratory circuit for a mechanical ventilator becomes abnormally large relative to a proportion of the lungs with intact air-exchanging parenchyma. Consequently, $CO_2$ removal is hampered and arterial $CO_2$ ($PaCO_2$) may increase. This causes the tidal volume and mechanical ventilation to increase in order to maintain a tolerable level of arterial pressure ($PaCO_2$).

Until recently, efforts had been made to minimize dead space, or dead volume, introduced in the respiratory circuit of mechanical ventilators. However traditional tubes, for example endotracheal tubes, and other devices of conventional mechanical ventilators used single lumen designs and contributed to dead space formation. For that reason, optimization of $CO_2$ removal was deficient.

Problems related to the presence of dead space induced by respiratory circuits of mechanical ventilators have been significantly reduced by the introduction of a patient-synchronized ventilatory assist system and method, including a feature of reduction of anatomical dead space in a patient's airways. This system and method are disclosed in International Application Publication no WO 2012/000096 A1 to Sinderby et al., published on Jan. 5, 2012, the disclosure of which is incorporated by reference herein in its entirety. The ventilatory assist system and method introduced by Sinderby supply ventilatory assist via an endotracheal tube structured for delivering a separate, unidirectional inspiratory air flow into the patient's trachea via a first inspiratory tube lumen and a separate, unidirectional expiratory air flow from the patient's trachea through a second expiratory tube lumen. Also, a unidirectional flow of air is produced and maintained through the inspiratory tube lumen and the expiratory tube lumen; in this manner, ventilatory circuit dead space is eliminated, anatomical dead space is substantially reduced and washing out of $CO_2$ is optimized.

Sinderby's method and system rely on a multi-lumen tube inserted into the trachea. The multi-lumen tube contains at least one inspiratory lumen as well as at least one second lumen, the latter constituting an expiratory lumen of the tube.

Due to risks of complications for the patient, it is often preferred not to change an already installed endotracheal tube of an intubated patient. It is also desired to control an amount of suppression of respiratory drive that occurs when applying the aforementioned method for patient-synchronized ventilatory assist with endotracheal through-flow.

Therefore, there is a need for improvements to current ventilatory assist systems and methods to maintain newly discovered advantages while mitigating potential complications to the patients.

SUMMARY

According to the present disclosure, there is provided a device for providing ventilatory assist to a patient. The device comprises a manifold including an inspiratory port connectable to an inspiratory supply line, an interface port connectable to an external end of an endotracheal tube and an expiratory port configured to receive an expiratory flow from the endotracheal tube via the interface port. The device also comprises an inspiratory lumen having a distal end insertable in the endotracheal tube towards a distal end thereof. A cross-section of the inspiratory lumen is less than a cross-section of the endotracheal tube. A valve is configured to direct an inspiratory flow from the inspiratory supply line to the inspiratory lumen, or to the endotracheal tube, or at once to the inspiratory lumen and to the endotracheal tube.

According to the present disclosure, there is also provided a system for providing ventilatory assist to a patient intubated with an endotracheal tube. The system includes the device for providing ventilatory assist to a patient. The system also comprises a controller configured to control the valve to direct an inspiratory flow from the inspiratory supply line to the inspiratory lumen, or to the endotracheal tube, or at once to the inspiratory lumen and to the endotracheal tube.

The present disclosure further relates to a method of providing ventilatory assist to a patient intubated with an endotracheal tube, comprising: providing ventilatory assist to the patient using the above described system; measuring a tidal volume of the patient; if the measured tidal volume of the patient is higher than a target tidal volume, increasing a fraction of the inspiratory flow delivered through the inspiratory lumen; and if the measured tidal volume of the patient is lower than the target tidal volume, decreasing the fraction of the inspiratory flow delivered through the inspiratory lumen.

Accordingly to another aspect, the present disclosure relates to a method of providing ventilatory assist to a patient intubated with an endotracheal tube, comprising: providing ventilatory assist to the patient using the above described system; measuring a tidal volume of the patient; if the measured tidal volume of the patient is higher than a target tidal volume, increasing a fraction of the inspiratory flow delivered through the inspiratory lumen; and if the measured tidal volume of the patient is lower than the target tidal volume, decreasing the fraction of the inspiratory flow delivered through the inspiratory lumen. Increasing or decreasing the fraction of the inspiratory flow delivered through the inspiratory lumen is performed in synchrony with a physiological signal indicative of the inspiratory effort of the patient.

According to a further aspect, the present disclosure is concerned with a system for providing ventilatory assist to a patient, comprising: a manifold including an inspiratory port configured to receive a first inspiratory flow from a first inspiratory supply line, an interface port connectable to an external end of an endotracheal tube, and an expiratory port configured to receive an expiratory flow from the endotracheal tube via the interface port; and an inspiratory lumen configured to receive a second inspiratory flow from a second inspiratory supply line, the inspiratory lumen having a distal end insertable via the interface port in the endotracheal tube, a cross-section of the inspiratory lumen being smaller than a cross-section of the endotracheal tube.

The present disclosure further relates to a method of providing ventilatory assist to a patient intubated with an endotracheal tube, the method comprising: providing ventilatory assist to the patient using the system described in the preceding paragraph, wherein the second inspiratory flow is a fraction of a total inspiratory flow including the first and second inspiratory flows; measuring a tidal volume of the patient; if the measured tidal volume of the patient is higher than a target tidal volume, increasing the fraction of the total inspiratory flow delivered through the inspiratory lumen; and if the measured tidal volume of the patient is lower than the target tidal volume, decreasing the fraction of the total inspiratory flow delivered through the inspiratory lumen.

According to a still further aspect, there is provided a manifold adapted for connection to a device for providing ventilator assist to a patient, comprising an inspiratory port connectable to an inspiratory supply line, a sealable port configured for insertion of an inspiratory lumen; an interface port connectable to an external end of an endotracheal tube; and an expiratory port configured to receive an expiratory flow from the endotracheal tube via the interface port.

The foregoing and other features will become more apparent upon reading of the following non-restrictive description of illustrative embodiments thereof, given by way of example only with reference to the accompanying drawings.

BRIEF DESCRIPTION OF THE DRAWINGS

Embodiments of the disclosure will be described by way of example only with reference to the accompanying drawings, in which.

Like numerals represent like features on the various Figures of the drawings.

DETAILED DESCRIPTION

Figure 1:
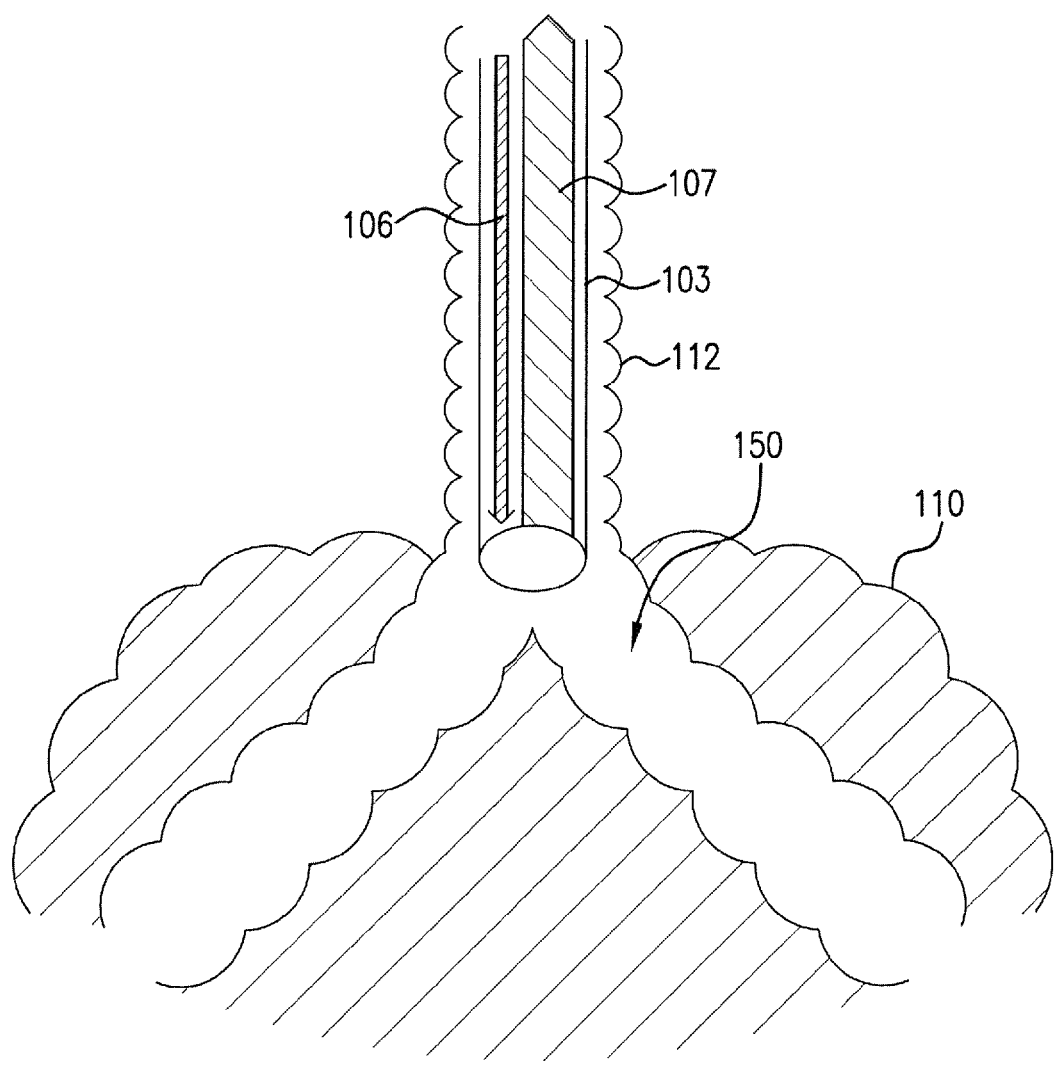
FIG. 1 is a side elevational, cross sectional partial view of an example of double-lumen endotracheal tube showing intratracheal pulmonary ventilation.

Various aspects of the present disclosure generally address one or more of the problems related to using a patient-synchronized ventilatory assist system and method as presented in the background of the present disclosure while mitigating potential complications to the patients. Specifically, the present disclosure addresses patient-synchronized ventilatory assist with endotracheal through-flow. The present technology favors a reduction of patient's rebreathing of extrapulmonary and instrumental dead space during patient-synchronized inspiratory assist.

For that purpose, the present disclosure introduces a device, a system and a method for providing ventilatory assist to a patient with endotracheal through-flow. The device can be connected to a conventional endotracheal tube and, as such, does not require replacing such tube if already installed on the patient.

The device, system and method are capable of controlling a reduction of patient's rebreathing of extrapulmonary and instrumental dead space. Generally stated, the ventilatory assist device can direct inspiratory and expiratory flows through a common endotracheal tube inserted in the patient's trachea. If the tidal volume of the patient exceeds a predetermined value, indicating the presence of excessive dead space potentially causing $CO_2$ rebreathing and increased inspiratory effort, a valve directs a portion or all of the inspiratory flow in a separate inspiratory lumen inserted within the endotracheal tube and having a tip positioned near a distal end of the endotracheal tube. This inspiratory lumen does not carry any part of the expiratory flow. This favors the elimination of excess $CO_2$ in the expiratory flow through the endotracheal tube.

A result of the reduction of dead space induced by the respiratory circuit of a mechanical ventilator is a reduction of the levels of respiratory drive, tidal volumes and mechanical ventilation, for example in critically ill patients. In this manner, mechanical ventilation may be used to efficiently unload the patient's respiratory system and respiratory muscles. Also, ventilatory $CO_2$ removal is optimized due to the reduction of dead space, limiting $CO_2$ rebreathing, which in turn reduces metabolic load.

The following terminology is used throughout the present disclosure:

Lung parenchyma: functional tissue of the lung.

Dead space: Amount of extrapulmonary volume, including anatomical volume of a patient's airway (exclusive of the lung parenchyma) and volume in the respiratory circuit of a mechanical ventilator.

Tidal volume: lung volume representing a volume of air displaced between inhalation and exhalation.

Ventilatory assist system: Apparatus adapted for medical use for assisting a patient in need of respiratory support.

Airway (of a patient): Lungs, bronchi, trachea, pharynx, nose, mouth, etc. through which air is breathed.

Air: Any gas composition suitable for use in a ventilatory assist system. In the context of the present disclosure, the term "air" may refer to natural air, pure oxygen, natural air enriched with added oxygen, oxygen mixed with another gases such as water vapor, or any combination thereof. This term may also refer to air expelled from a patient's lungs, for example natural air containing additional $CO_2$ and humidity.

Lumen: A bore of a tube, for example a respiratory tube. A given tube may comprise a plurality of lumens.

Physiological signal: A measurable biometric quantity capable of being transmitted, for example an electrical signal, such as a physiological breathing signal generated by respiratory muscles.

Inspiratory effort: Voluntary or involuntary exertion of breathing by a patient. This may be quantified as a neural measure.

Restricted/unrestricted: In the context of the present disclosure, an air flow present in a tube, lumen, or like conduit may be subject to a variable resistance, or restriction. It is well-known to those skilled in the art of fluid mechanics that any conduit will apply at least a minimum resistance to a flow. The terms "unrestricted" and "restricted" should be understood as relative terms expressing, respectively, a lower and a higher resistance to air flow.

Minimum air flow: A partially restricted, non-zero air flow.

Endotracheal: Of a tube adapted for placement into a patient's trachea.

Synchrony: Time-wise correspondence between events.

In an aspect, mechanical ventilation may be synchronized with patient's effort to breathe. For example, a physiological breathing signal is used to regulate the ventilatory assist in synchrony with the patient's neural inspiration effort, thereby unloading and compensating for weak respiratory muscles. The present ventilatory assist device may therefore be used with a system having an inspiratory supply line for providing breathing gas to the patient and controlling the portions of the inspiratory flow that are directed in the common endotracheal tube and/or in the inspiratory lumen. An example of such a system will be described with reference to FIGS. 1, 2 and 3.

FIG. 1 is a side elevational, cross sectional partial view of an example of double-lumen endotracheal tube showing intratracheal pulmonary ventilation. A double-lumen endotracheal tube 103 as shown on FIG. 1 forms part of a ventilatory assist system for delivering air to the lungs 110 of a patient via the trachea 112 as described in International Application Publication no WO 2012/000096 A1 to Sinderby et al., published on Jan. 5, 2012, the disclosure of which is incorporated by reference herein in its entirety. Schematically shown in FIG. 1 are an inspiratory flow in direction 106 toward the patient's lungs 110 and an expiratory flow in direction 107 away from the patient's lungs 110, through the double-lumen endotracheal tube 103 inserted into the patient's trachea 112. Direction 106 is shown as a narrow arrow while direction 107 is shown as a thick arrow; this should be understood as a schematic illustration that the inspiratory flow in direction 106 originates from a smaller-diameter inspiratory tube lumen (also shown in FIG. 3) while the expiratory flow in direction 107 is conducted through a larger-diameter expiratory tube lumen (also shown in FIG. 3).

Figure 2:
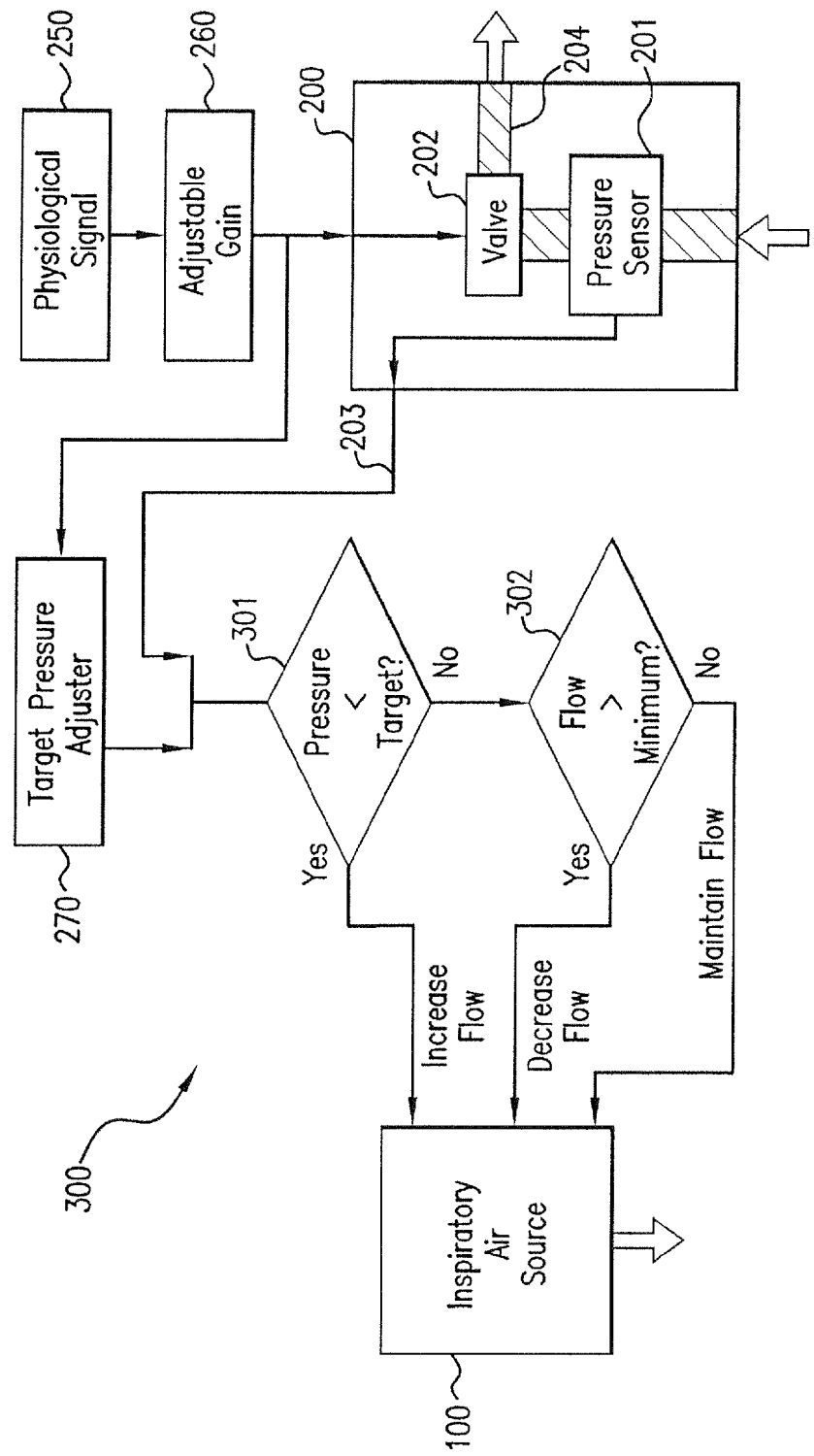
FIG. 2 is a block diagram of a pressure feedback system for use in a ventilatory assist system with the double-lumen endotracheal tube of FIG. 1.

FIG. 2 is a block diagram of a pressure feedback system for use in a ventilatory assist system with the double-lumen endotracheal tube of FIG. 1. Later Figures will show how the double-lumen endotracheal tube 103 of FIG. 1 may be substituted by a ventilatory assist device having a manifold connectable to a conventional endotracheal tube and an inspiratory lumen insertable in the conventional endotracheal tube.

Figure 3:
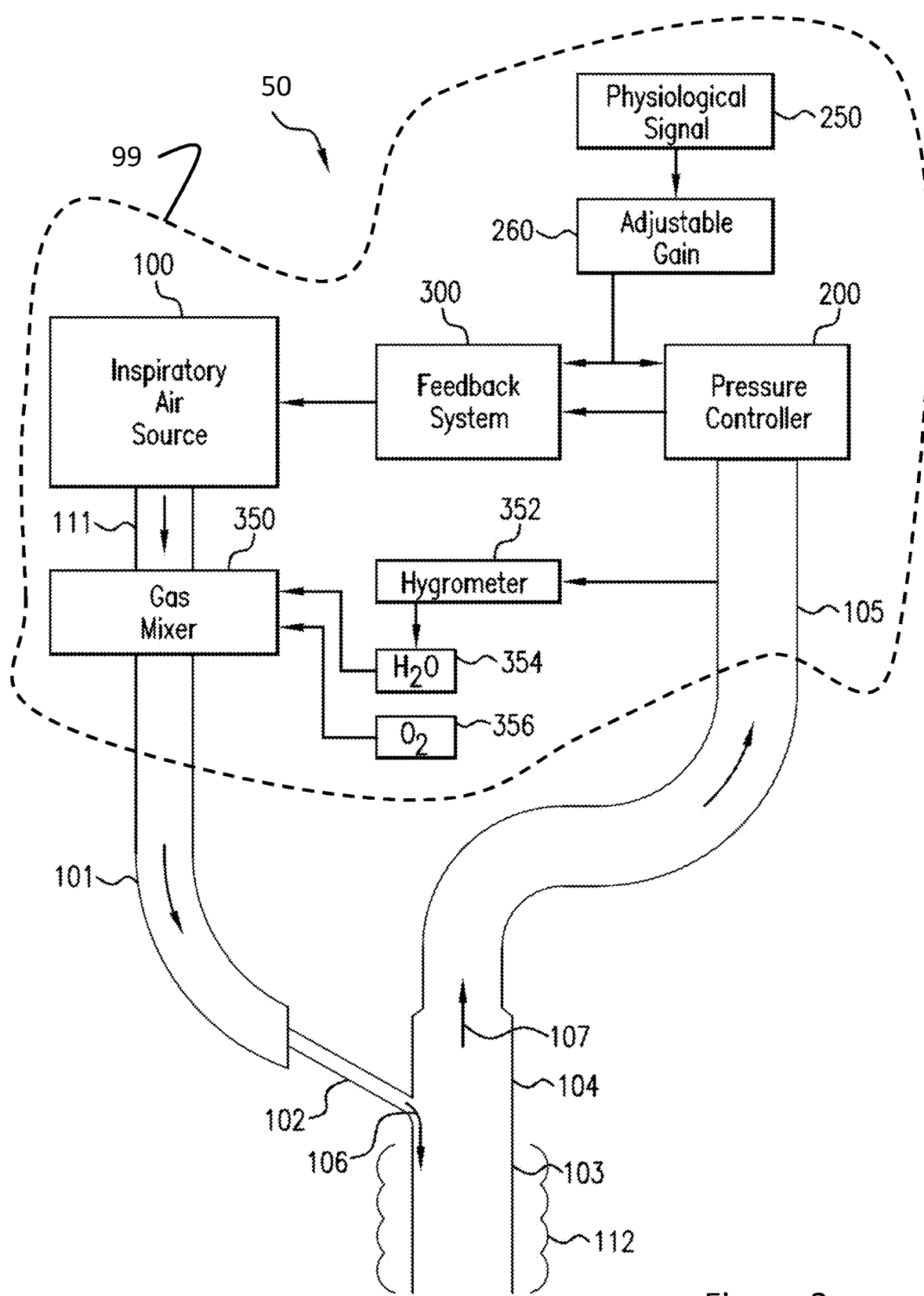
FIG. 3 is an example a ventilatory assist system integrating the double-lumen endotracheal tube of FIG. 1 with the pressure feedback system of FIG. 2.

The pressure feedback system 300 of FIG. 2 for controlling an inspiratory flow was also introduced in International Application Publication no WO 2012/000096 A1. FIG. 3 is an example of a ventilatory assist system integrating the double-lumen endotracheal tube of FIG. 1 with the pressure feedback system of FIG. 2. The following description will refer to FIGS. 2 and 3 concurrently.

The ventilatory assist system 50 shown on FIG. 3 comprises a pressure control system 99 connected to the double-lumen endotracheal tube 103 via an inspiratory supply line 101 and via an expiratory line 105. The pressure control system 99 includes an inspiratory air source 100, the pressure feedback system 300 and a pressure controller 200. The pressure feedback system 300 and the pressure controller 200 may both be responsive to a physiological breathing signal 250, which may be altered by a gain adjuster 260 in some embodiments. The pressure control system 99 may further include a hygrometer 352, a humidifier 354, an oxygen source 356, and a gas mixer 350.

The inspiratory air source 100 has an outlet 111 connected to the inspiratory supply line 101 through the gas mixer 350, if present. The inspiratory air source 100 generates an air pressure, volume or flow to produce a target air flow through the inspiratory supply line 101. The inspiratory supply line 101 is in turn connected to an inspiratory tube lumen 102 of the double-lumen endotracheal tube 103 that is inserted into the patient's trachea 112. The inspiratory tube lumen 102 may be a single or multiple lumen.

A second lumen of the double-lumen endotracheal tube 103, hereinafter referred to as an expiratory tube lumen 104, is connected to the expiratory line 105 itself connected to the pressure controller 200. An example of pressure controller 200 may include, as illustrated in FIG. 2, a pressure sensor 201 and a valve 202 connected to an exhaust 204 to regulate air flow through the expiratory tube lumen 104 and the expiratory line 105. The pressure controller 200 may be feedback operated to produce and maintain a given pressure in the expiratory tube lumen 104 and the expiratory line 105. As will be described in more detail in the following description, the valve 202 may be controlled by the physiological breathing signal 250 for synchronizing the air flow through the expiratory tube lumen 104 and the expiratory line 105 with this physiological breathing signal 250. The pressure controller 200 operates in such a manner that the valve 202 restricts, but does not completely occlude the expiratory line 105 such that a minimum outward air flow remains present in the expiratory tube lumen 104 and the expiratory line 105 during the patient's inspiratory phase. Modulation of the restriction of the air flow through the expiratory tube lumen 104 allows adjustment of the pressure in the respiratory circuit of the mechanical ventilator to be, for example, proportional to the physiological breathing signal 250. A lowest pressure limit may be manually set to ensure sufficient positive end-expiratory pressure (PEEP) to maintain lung recruitment during neural expiration.

More specifically, the inspiratory air source 100 generates a target air flow through the inspiratory supply line 101 and the inspiratory tube lumen 102. In turn, the pressure controller 200 regulates a pressure for controlling air flow escaping the trachea 112 and the patient's lungs 110 through the expiratory tube lumen 104 and the expiratory line 105; specifically, the pressure controller 200 uses the valve 202 to alter a resistance to air flow of the expiratory tube lumen 104 and expiratory line 105.

The problem of limiting air flow resistance through the expiratory tube lumen 104 and the expiratory line 105 is resolved by providing the expiratory tube lumen 104 with a diameter larger than that of the inspiratory tube lumen 102. The larger resistance to air flow of the smaller-diameter inspiratory tube lumen 102 causes a larger pressure drop. However, the effect of this larger pressure drop is compensated for by using the inspiratory air source 100 to generate a target air flow through the inspiratory tube lumen 102.

The pressure feedback system 300 between the pressure controller 200 and the inspiratory air source 100 ensures that the target air flow through the inspiratory supply line 101 and inspiratory tube lumen 102 is adjusted to generate a preset target pressure in the trachea 112, the expiratory tube lumen 104 and the expiratory line 105. The pressure feedback system 300 comprises, as shown in FIG. 2, a first comparator 301 and an optional second comparator used as a minimum flow detector 302. The comparator 301 may receive a target pressure signal from a target pressure adjuster 270.

The target pressure adjuster 270 is responsive to the physiological breathing signal 250 to adjust the level of a target pressure. The physiological breathing signal 250 is a physiological signal as defined hereinabove. It may be reliably obtained as a measure of the electrical activation of the patient's diaphragm (EAdi), obtained for example using a method as described in U.S. Pat. Nos. 5,671,752, 5,820,560, 6,588,423, 6,901,286 and 7,661,427, the disclosures of which are incorporated by reference herein in their entirety. The physiological breathing signal 250 may alternatively take the form of an electromyogram (EMG) signal obtained at the level of the alea of the nose (EMG-AN) of the patient, or at the thorax level (EMG-THO) of the patient. Biometric signals from the phrenical nerve of the patient, surface EMG, or measures of chest wall movements of the patient may also be used. Of course any other suitable physiological breathing signal 250 indicative of inspiratory flow, pressure and/or effort, including onset detection of the inspiratory effort before the generation of inspiratory flow occurs, may be used. For example, the target pressure adjuster 270 may increase the level of the target pressure when the level of the physiological breathing signal 250 increases, indicating an increase of the patient's inspiratory effort. In the same manner, the adjuster 270 may decrease the level of the target pressure when the level of the physiological breathing signal 250 decreases, indicating a decrease of the patient's inspiratory effort. In fact, the target pressure may be adjusted by the target pressure adjuster 270 in proportion to the level of patient's inspiratory activity as indicated by the level of the physiological breathing signal 250 or in any other manner beneficial to patient's inspiratory assist. In an embodiment, the target pressure may further be set to ensure sufficient positive end-expiratory pressure (PEEP). Obviously, the target pressure adjuster 270 may also be set at a single level independent of the physiological breathing signal 250.

Operation of the pressure feedback system 300 follows the following rules:

The target air flow through the inspiratory supply line 101 and inspiratory tube lumen 102 is increased by the inspiratory air source 100 when the comparator 301 detects that the pressure reading 203 from the pressure sensor 201 of the pressure controller 200, indicative of the pressure in the trachea 112, expiratory tube lumen 104 and expiratory line 105 during the patient's inspiration phase is lower than the target pressure from the target pressure adjuster 270.

The target air flow through the inspiratory supply line 101 and inspiratory tube lumen 102 is decreased by the inspiratory air source 100 when the comparator 301 detects that the pressure reading 203 from the pressure sensor 201 of the pressure controller 200, indicative of the pressure in the trachea 112, expiratory tube lumen 104 and expiratory line 105 during the patient's inspiration phase is higher than the target pressure from the target pressure adjuster 270, and also if it is higher than the manually set PEEP level. Before decreasing the target air flow through the inspiratory supply line 101 and inspiratory tube lumen 102, the minimum flow detector 302 ensures that the inspiratory air source 100 maintains a target air flow, through the inspiratory supply line 101 and inspiratory tube lumen 102, that is at least equal to or higher than a minimum value. If not, the current target air flow through the inspiratory supply line 101 and inspiratory tube lumen 102 is maintained. The minimum value used in the minimum flow detector 302 for the target air flow is selected to be sufficient to ensure continuous washing out of $CO_2$.

Operation of the pressure feedback system 300 may be synchronized using the physiological breathing signal 250. More specifically, the valve 202 of the pressure controller 200 will partially close when the physiological breathing signal 250 indicates patient's inspiratory effort to allow the target air flow from the inspiratory supply line 101 and the inspiratory tube lumen 102 to build up a pressure in the endotracheal tube 103, the expiratory tube lumen 104 and the expiratory line 105 in order to assist inspiration of the patient. The valve 202 is partially closed to maintain a minimum air flow through the expiratory tube lumen 104 and the expiratory line 105 to contribute to, if not completely eliminate, substantially reduce ventilatory circuit dead space and anatomical dead space, and ensure continuous washing out of $CO_2$. When the physiological breathing signal 250 no longer indicates inspiratory effort of the patient, the valve 202 is opened to an extent that allows the patient to expire through the double-lumen endotracheal tube 103, the expiratory tube lumen 104, the expiratory line 105, the valve 202 and the exhaust 204 while maintaining a certain level of expiratory pressure to prevent, for example, collapse of the lungs.

It should be understood that, during both the inspiration and expiration phases, a unidirectional air flow is produced through the inspiratory supply line 101, the inspiratory tube lumen 102, the expiratory tube lumen 104 and the expiratory line 105 to prevent air expired by the patient to be breathed again. In this manner, ventilatory circuit dead space and anatomical dead space are, if not completely eliminated, substantially reduced and continuous washing out of $CO_2$ is ensured.

In an embodiment, the gain adjuster 260 may alter the physiological breathing signal 250 to adjust the level of the pressure in the trachea 112, expiratory tube lumen 104 and expiratory line 105, and thereby adjust the level of ventilatory assist to the patient. For example, the adjustable gain 260 may be manually set by the medical personnel. Automatic adjustment of the gain 260 may also be contemplated, for example to obtain a target level of ventilatory assist or physiological breathing signal 250.

Some options, amongst others, to deliver inspiratory assist to the patient are the following:

A target pressure or volume may be supplied to the patient during inspiration.

As explained in the foregoing description, the target pressure may be adjusted by the target pressure adjuster 270 in proportion to the level of patient's inspiratory activity as indicated by the level of the physiological breathing signal 250 or in any other manner beneficial to patient's inspiratory assist.

A mathematical model may be used for calculating a pressure loss within the endotracheal tube 103 based on a known air flow resistance and the diameters of the endotracheal tube 103, the expiratory tube lumen 104 and the expiratory line 105, and on a measurement of the air flow through these endotracheal tube 103, the expiratory tube lumen 104 and the expiratory line 105. The calculated pressure loss may then serve as the target pressure used by the comparator 301.

Another option is to directly measure a pressure at the free, proximal end of the endotracheal tube 103 inserted into the patient's trachea 112, near the tracheal bifurcation 150 (FIG. 1), and use this pressure as the target pressure of the comparator 301.

Oxygen from the oxygen source 356 may be injected in the inspiratory supply line 101 through the gas mixer 350 to enrich the target air flow through the inspiratory supply line 101 and inspiratory tube lumen 102.

In an embodiment, to ensure adequate humidification, the humidity sensor (hygrometer) 352 may be used to detect humidity in the expiratory line 105 and, in response to the detected humidity, control the humidifier 354 connected to the gas mixer 350 to humidify, whenever needed, the target air flow through the inspiratory supply line 101 and the inspiratory tube lumen 102.

Some of the modules of FIGS. 2 and 3 may be combined in a same analog or digital hardware module. In some embodiments, some of these modules may be realized in the form of hardware devices while other modules may be realized as computer executable instructions. All possible analog hardware and/or digital hardware (including any kind of computers and processors) and/or software combinations of those modules are within the scope of the present disclosure.

Figure 4:
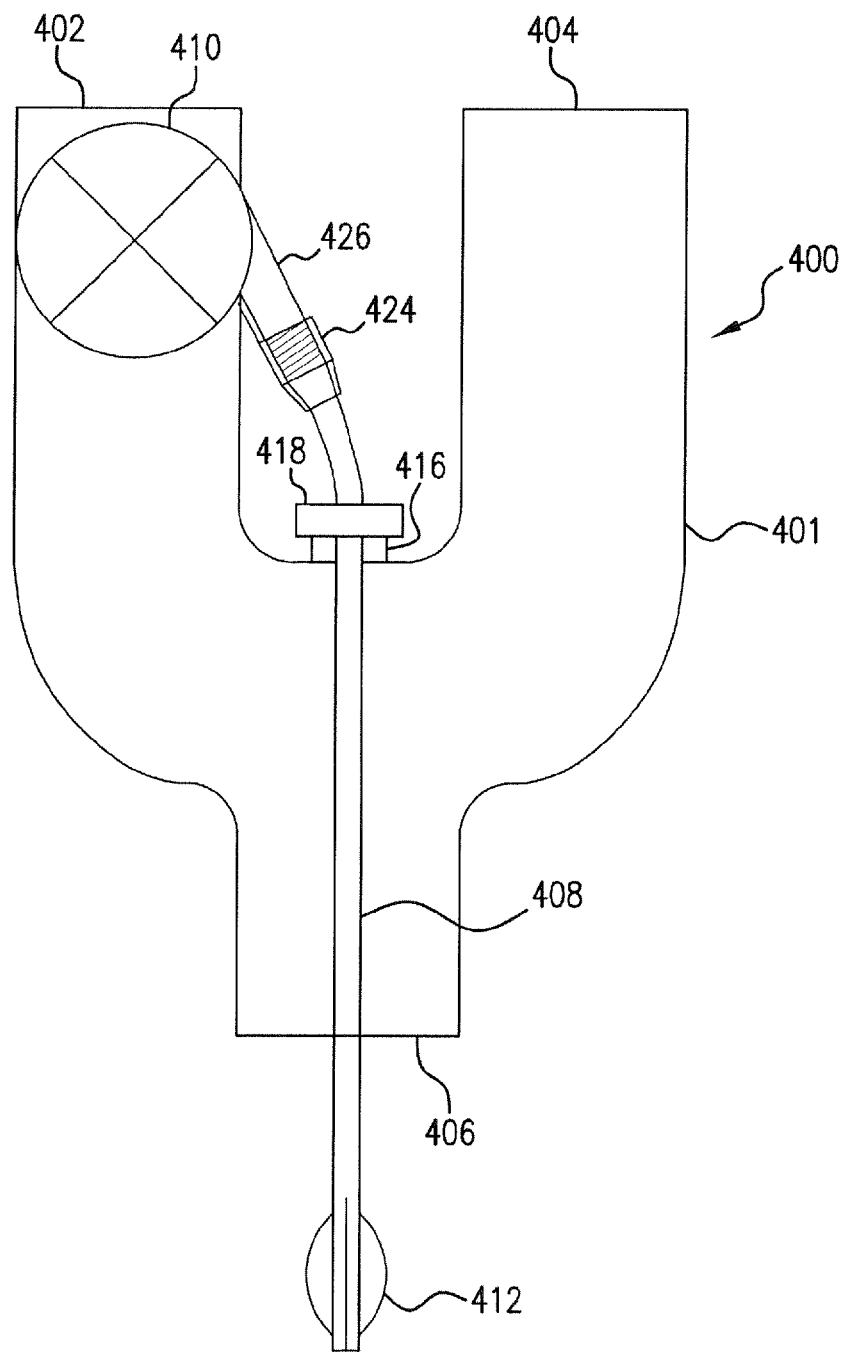
FIG. 4 is a schematic, side elevational view of a device usable to replace the double-lumen endotracheal tube of FIG. 1.
Figures 5, 6, 7:
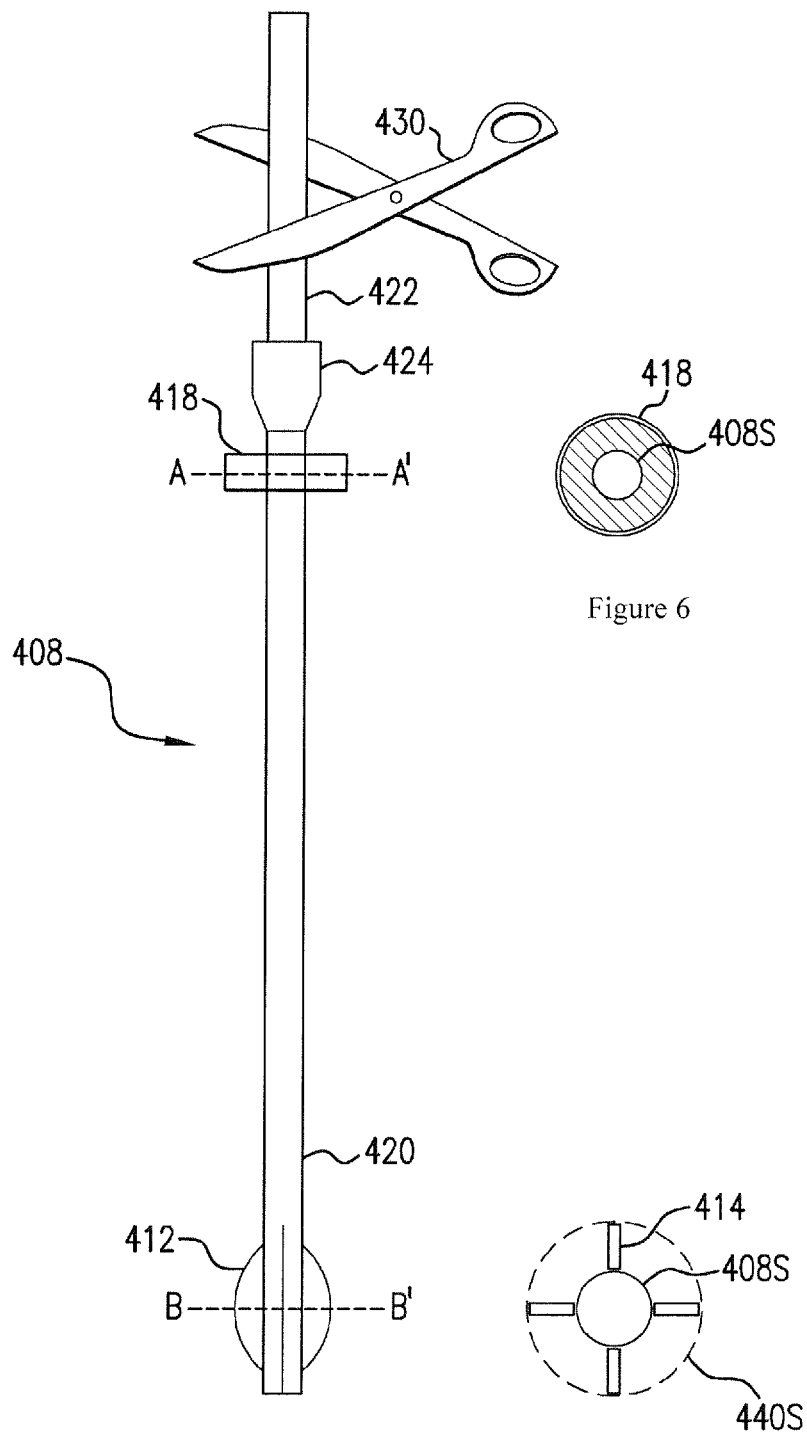
FIG. 5 is a schematic, side elevational view of an inspiratory lumen of the device of FIG. 4.
FIG. 6 is a cross sectional view of the inspiratory lumen of FIG. 5 taken at the level of an external plug.
FIG. 7 is a cross sectional view of the inspiratory lumen of FIG. 5 taken at the level of a distal projection.

As expressed hereinabove, it is often preferred not to replace an already installed endotracheal tube of an intubated patient. To this end, FIG. 4 is a schematic view of a device usable to replace the double-lumen endotracheal tube of FIG. 1. FIG. 5 is a schematic view of an inspiratory lumen of the device of FIG. 4. FIG. 6 is a cross sectional view of the inspiratory lumen of FIG. 5 taken at the level of an external plug. FIG. 7 is a cross sectional view of the inspiratory lumen of FIG. 5 taken at the level of a distal projection. The view of FIG. 6 is taken along line A-A' of FIG. 5 while the view of FIG. 7 is taken along line B-B' of FIG. 5.

Referring at once to FIGS. 4-7, a device 400 comprises a manifold 401 having an inspiratory port 402 connectable to the inspiratory supply line 101, an expiratory port 404 connectable to the expiratory line 105, an interface port 406 connectable to an external end 442 (FIG. 8) of an endotracheal tube 440. The device 400 also comprises an inspiratory lumen 408 having a distal end 420 insertable in the endotracheal tube 440 towards a distal end 444 thereof. A cross-section 408S of the inspiratory lumen 408 is smaller than a cross-section 440S of the endotracheal tube 440 so that the inspiratory lumen 408 can easily be installed within the endotracheal tube 440 when the patient is already intubated. The device 400 further comprises a valve 410 positioned within the manifold 401, downstream of the inspiratory port 402, and configured to direct an inspiratory flow from the inspiratory supply line 101 to the inspiratory lumen 408, or to the endotracheal tube 440 through the manifold 401 and the interface port 406, or at once to the inspiratory lumen 408 and to the endotracheal tube 440, in variable fractions. The skilled reader will appreciate that in the foregoing, the inspiratory flow in the endotracheal tube 440 actually refers to a flow that surrounds the inspiratory lumen 408, which is itself inserted in the endotracheal tube 440, and excludes the inspiratory flow within the inspiratory lumen 408. As shown, the inspiratory lumen 408 comprises distal projections 412, for example a set of four radial distal projections 412 disposed longitudinally and 90° apart from each other, and configured to maintain the distal end 420 of the inspiratory lumen 408 substantially centered within the cross-section 440S of the endotracheal tube 440. It should be noted that the various Figures are not to scale. Specifically, the distal projections 412 are formed by a plurality, for example four 90° angularly spaced-apart, longitudinally oriented radial wings 414 protruding from a main tube of the inspiratory lumen 408, the radial wings 414 being sized to substantially abut an internal wall of the endotracheal tube 440 without impeding a gas flow in the endotracheal tube 440. Though only one set of distal projections 412 is shown on the various Figures, a plurality of sets of distal projections 412 may be provided along the length of the distal end 420 of the inspiratory lumen 408.

The manifold 401 also has a sealable port 416 configured for insertion of the distal end 420 of the inspiratory lumen 408. In turn, the inspiratory lumen 408 comprises an external plug 418, for example made of resilient plastic or rubber material, and separating a proximal end 422 of the inspiratory lumen 408 from its distal end 420. The plug 418 is configured to lock in the sealable port 416 without impeding any gas flow within the inspiratory lumen 408.

The valve 410 has a valve outlet 426 external from the manifold 401 and configured to direct at least in part the inspiratory flow to the valve outlet 426. The proximal end 422 of the inspiratory lumen 408 is configured to connect to the inspiratory port 402 through the valve outlet 426. The proximal end 422 of the inspiratory lumen 408 may be provided with a length that can be cut using ordinary scissors such as 430 to adjust to a position of the valve outlet 426 when the plug 418 is locked in the sealable port 416. An internally threaded connector 424 may be screwed on an externally threaded free end portion of the valve outlet 426 to ensure that the connection of the valve outlet 426 to the proximal end 422 of the inspiratory lumen 408 is properly sealed.

The valve 410 is configured to adjust fractions of the inspiratory flow in the inspiratory lumen 408 and in the endotracheal tube 440 for controlling the tidal volume of the patient. In particular, the valve 410 can adapt the fractions of inspiratory flow as a function of respective resistances of the inspiratory lumen 408 and of the endotracheal tube 440 or, more specifically, of remaining space within the endotracheal tube 440 when a part of its cross section 440S is occupied by the inspiratory lumen 408. The valve 410 may also be configured to modulate a pressure of the inspiratory flow to a physiological signal indicative of an inspiratory effort of the patient, or to synchronize the inspiratory flow to the physiological signal, the physiological signal being provided by a ventilatory assist system, including in a non-limitative example the ventilatory assist system 50 illustrated in FIG. 3. To this end, the physiological breathing signal 250 may, for example, be used as a synchronization signal.

Figure 8:
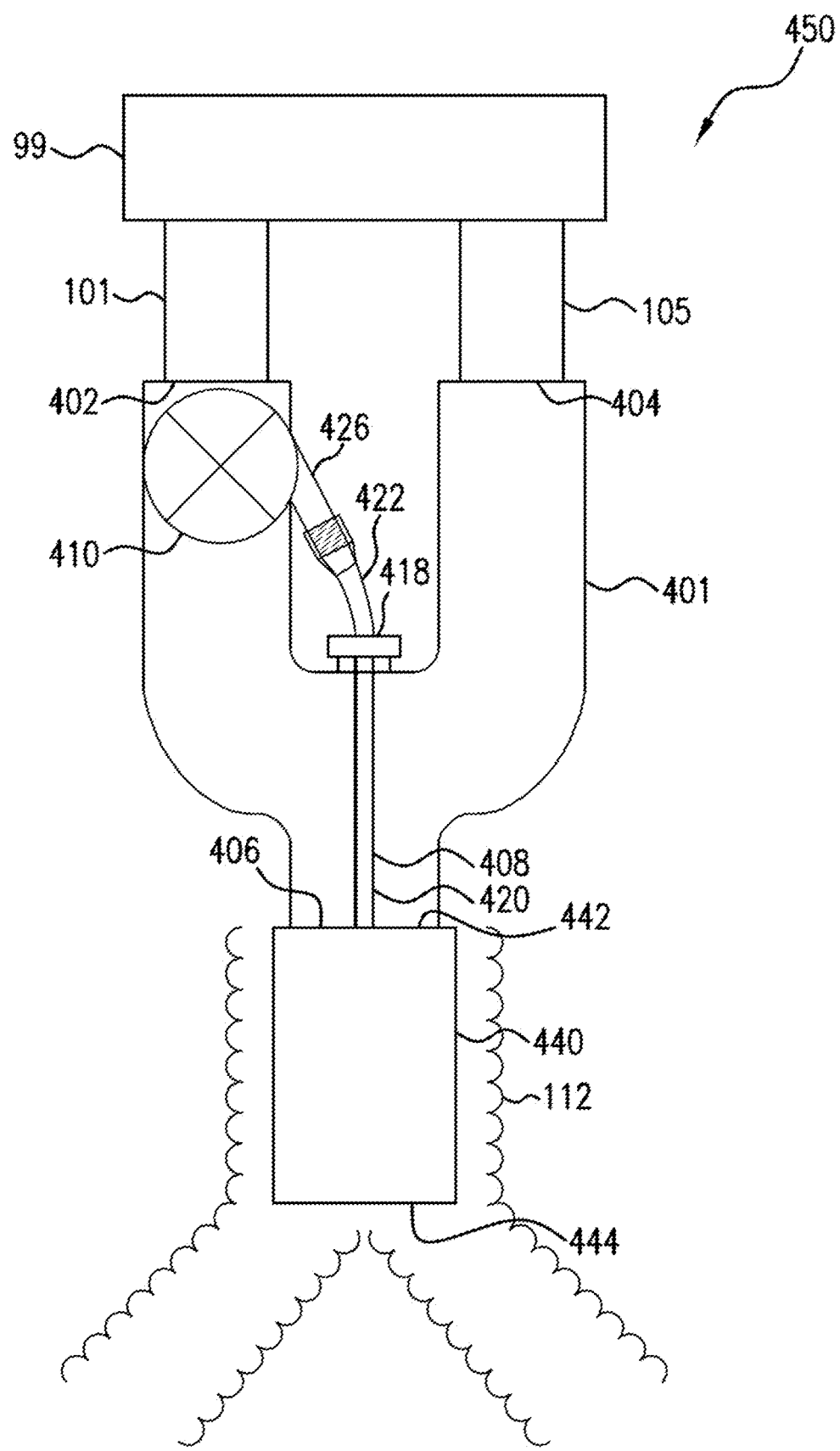
FIG. 8 is a side elevational view of a variant of the ventilatory assist system of FIG. 3, in which the device of FIG. 4 replaces the double-lumen endotracheal tube of FIG. 1.

FIG. 8 is a variant of the ventilatory assist system of FIG. 3, in which the device of FIG. 4 replaces the double-lumen endotracheal tube of FIG. 1. A system 450 for providing ventilatory assist to a patient intubated with an endotracheal tube comprises the device 400 connected to the pressure control system 99 (see also FIG. 3) via the inspiratory supply line 101 and the expiratory line 105. The inspiratory supply line 101 is connected to the inspiratory port 402 and the expiratory line 105 is connected to the expiratory port 404. A controller controls the valve 410 to direct an inspiratory flow from the inspiratory supply line 101 to the inspiratory lumen 408, or to the endotracheal tube 440 through the interface port 406, or at once to the inspiratory lumen 408 and to the endotracheal tube 440, in various fractions, to reduce the amount of dead space and control the patient's tidal volume. In the particular example of FIG. 8, the controller comprises the pressure feedback system 300 of FIGS. 2 and 3, which may further be configured to cause the valve 410 to modulate a pressure of the inspiratory flow according to, for example, a physiological or neural signal indicative of an inspiratory effort of the patient, or to cause the valve 410 to synchronize the inspiratory flow with the physiological signal indicative of an inspiratory effort of the patient, based on one or a combination of an electrical activation of the patient's diaphragm (EAdi), an electromyogram (EMG) signal, an expiratory pressure, an expiratory flow, an inspiratory flow, an inspiratory pressure, an end tidal carbon dioxide value, and an arterial carbon dioxide pressure. Without limitation, the valve 410 may modify the fractions of the inspiratory flow in the inspiratory lumen 408 and in the endotracheal tube 440 in synchrony with inspiratory phases, for example adjusting these fractions once every inspiratory phase or once every three (3) inspiratory phases. As in the case of FIG. 3, the expiratory port pressure controller 200 may use the physiological breathing signal representative of the patient's inspiratory effort and may be configured to allow an unrestricted air flow through the expiratory port 404 during the patient's expiration phase and to partially restrict the air flow through the expiratory port 404 to a minimum air flow during the patient's inspiration phase. In this way a unidirectional air flow can be produced through the inspiratory lumen 408 and in the manifold 401 towards the expiratory port 404 and through the manifold 401 from the inspiratory port 402 to the expiratory port 404 during both the patient's inspiration and expiration phases to prevent air expired by the patient from being breathed again.

Figure 9:
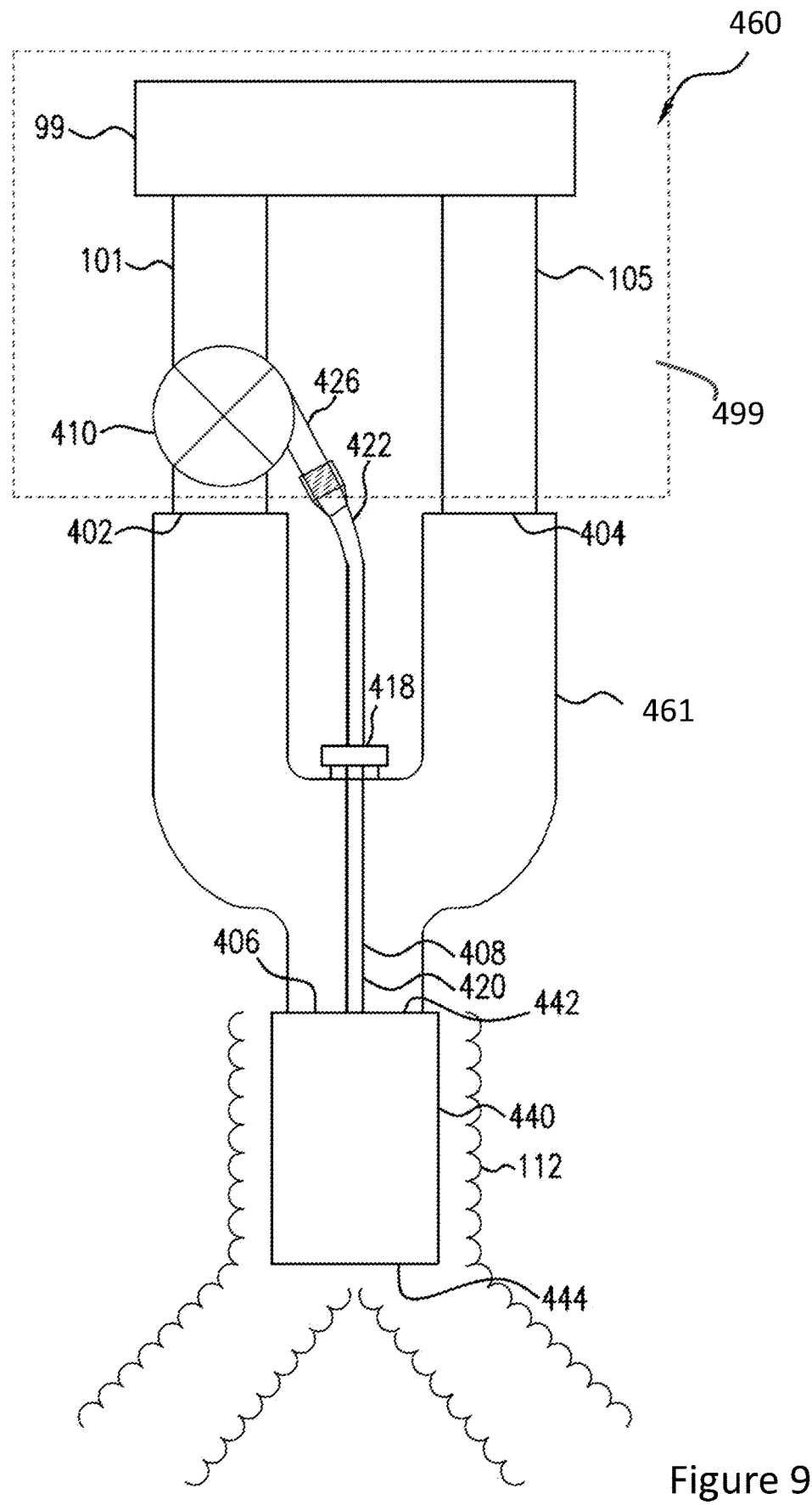
FIG. 9 is a side elevational view of a first variant of the ventilatory assist system of FIG. 8, in which a valve of the device of FIG. 4 is moved upstream of a manifold.

FIG. 9 is a side elevational view of a first variant of the ventilatory assist system of FIG. 8, in which a valve of the device of FIG. 4 is moved upstream of a manifold. The system 460 of FIG. 9 differs from the system 450 of FIG. 8 in that the valve 410 is located within the inspiratory supply line 101, upstream of the inspiratory port 402 of manifold 461 (identical to manifold 401 but without the valve 410). In the first variant of FIG. 9, the valve 410 may be located at any point between the inspiratory port 402 and the gas mixer 350 (if present), or at any point between the inspiratory port 402 and the inspiratory air source 100. For example, the valve 410 may be positioned on the inspiratory supply line 101 (a) between the inspiratory port 402 of the manifold 461 and a mechanical ventilator or (b) inside the mechanical ventilator 499 (shown in dashed line in FIG. 9). The placement of the valve 410 as shown on FIGS. 8 and 9 does not change the operation of the systems 450 and 460.

Figure 10:
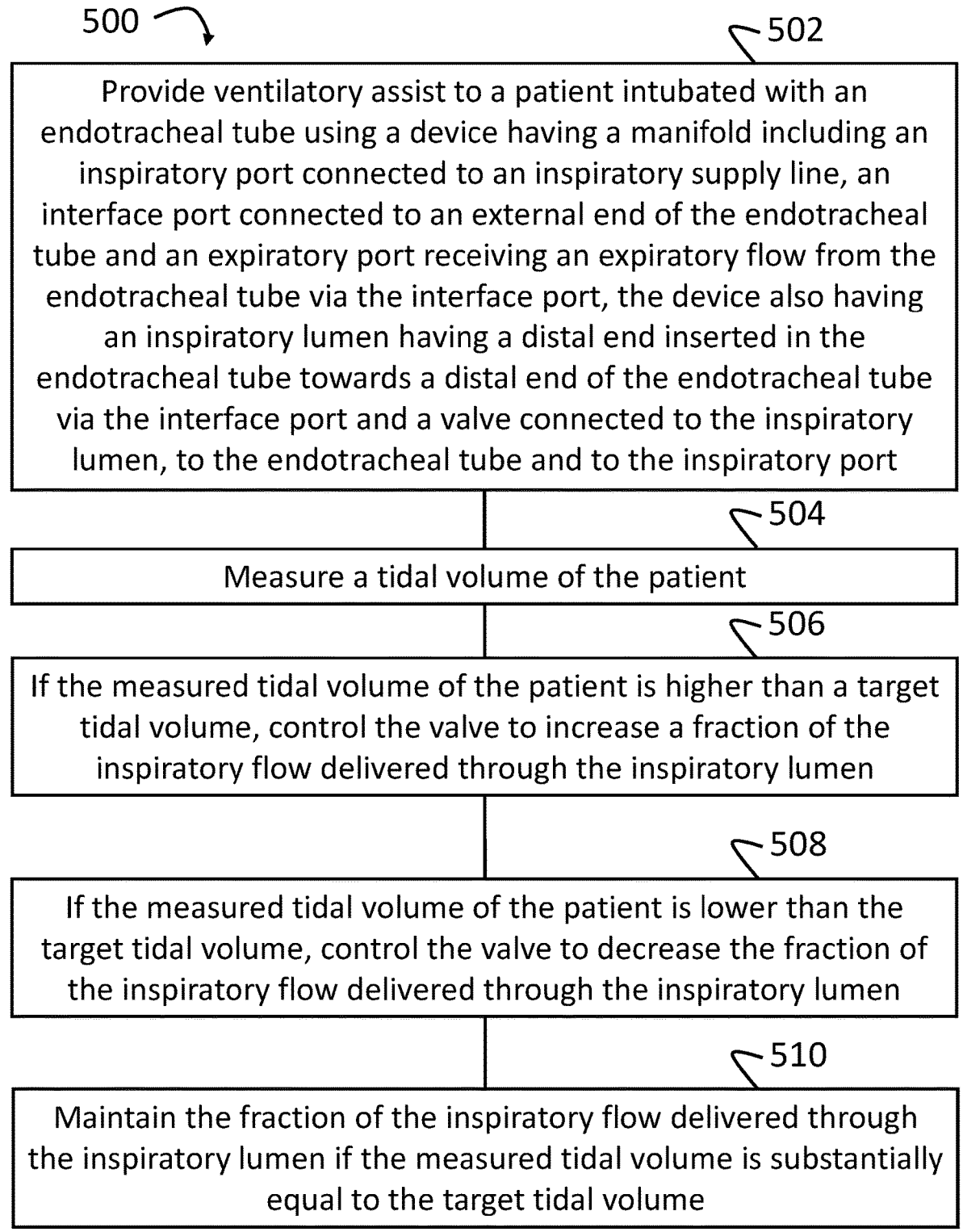
FIG. 10 is a flow chart showing operations of a method of using one of the systems of FIGS. 8 and 9.

FIG. 10 is a flow chart showing operations of a method of using one of the systems of FIGS. 8 and 9. The flow chart includes a sequence 500 comprising a plurality of operations that may be executed once or repeatedly, at regular intervals or as needed, in variable order, some of the operations possibly being executed concurrently, some of the operations being optional.

Operation 502 of FIG. 10 comprises providing ventilatory assist to an intubated patient using one of the systems of FIGS. 8 and 9, and the device of FIG. 4.

A tidal volume of the patient is measured at operation 504, for example being determined during conventional inspiratory-synchronized assist delivery by a pneumotachograph situated at the level of the endotracheal tube 440. Alternatively, measuring and integrating inspiratory and expiratory flows to deduce the tidal volume is also contemplated.

Verification is made at operation 506 to determine if the measured tidal volume of the patient is higher than a target tidal volume, in which case the valve 410 is controlled to increase a fraction of the inspiratory flow delivered through the inspiratory lumen 408. Of course, a remaining fraction of the inspiratory flow from the valve 410, if any, then flows through the manifold 401, the interface port 406, and the endotracheal tube 440.

At operation 508, if the measured tidal volume of the patient is lower than the target tidal volume, the valve 410 is controlled to decrease the fraction of the inspiratory flow delivered through the inspiratory lumen 408 while increasing the remaining fraction from the valve 410 flowing through the manifold 401, the interface port 406, and the endotracheal tube 440.

If the measured tidal volume is substantially equal to the target tidal volume, the fraction of the inspiratory flow delivered through the inspiratory lumen 408 is maintained at operation 510.

Using the method of FIG. 10, in a case the tidal volume is considered too large, extrapulmonary dead-space elimination is applied in order to reduce inspiratory effort, and hence, to reduce the tidal volume. However, applying extrapulmonary dead-space elimination to every breath may reduce the tidal volume more than necessary. Hence, feedback is used to target an average tidal volume. A ratio of breaths using conventional ventilation and extrapulmonary dead-space elimination is adjusted by operation of the valve 410. Increasing a flow through the inspiration lumen 408 increases the ratio of assisted breaths with extrapulmonary dead-space elimination until the target tidal volume has been achieved. If tidal volume is substantially at the target, the ratio of assisted breaths with extrapulmonary dead-space elimination is maintained. If the tidal volume becomes lower than the set target, the ratio of assisted breaths with extrapulmonary dead-space elimination is decreased in steps until the tidal volume is within an acceptable range.

Using the method of FIG. 10, the system of FIG. 8 or 9, or the device of FIG. 4, a practitioner can reduce ventilatory circuit dead space and anatomical dead space of a patient and thereby effectively control an amount of suppression of respiratory drive.

Figure 11:
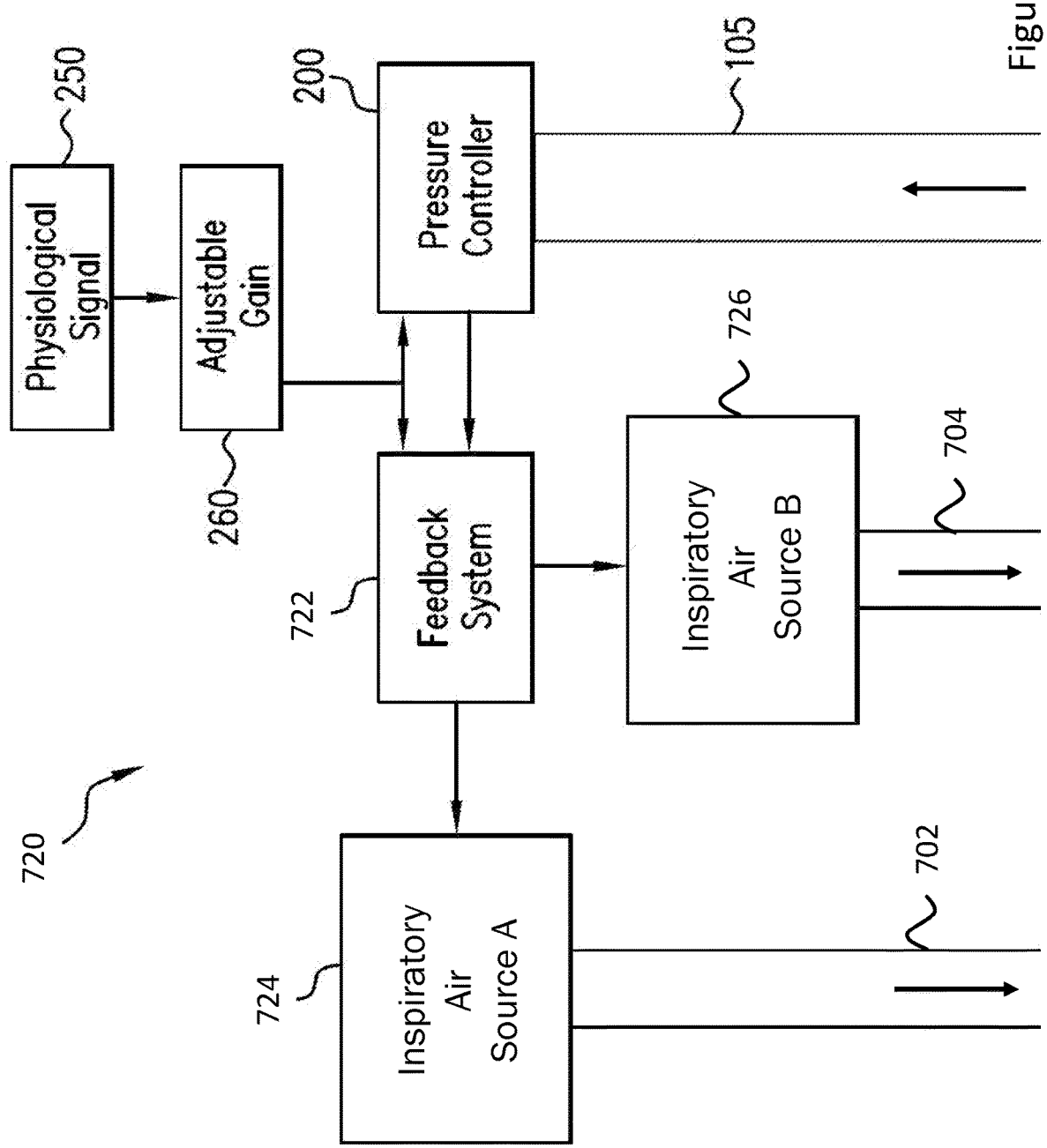
FIG. 11 is a block diagram of a pressure control system according to an embodiment.
Figure 12:
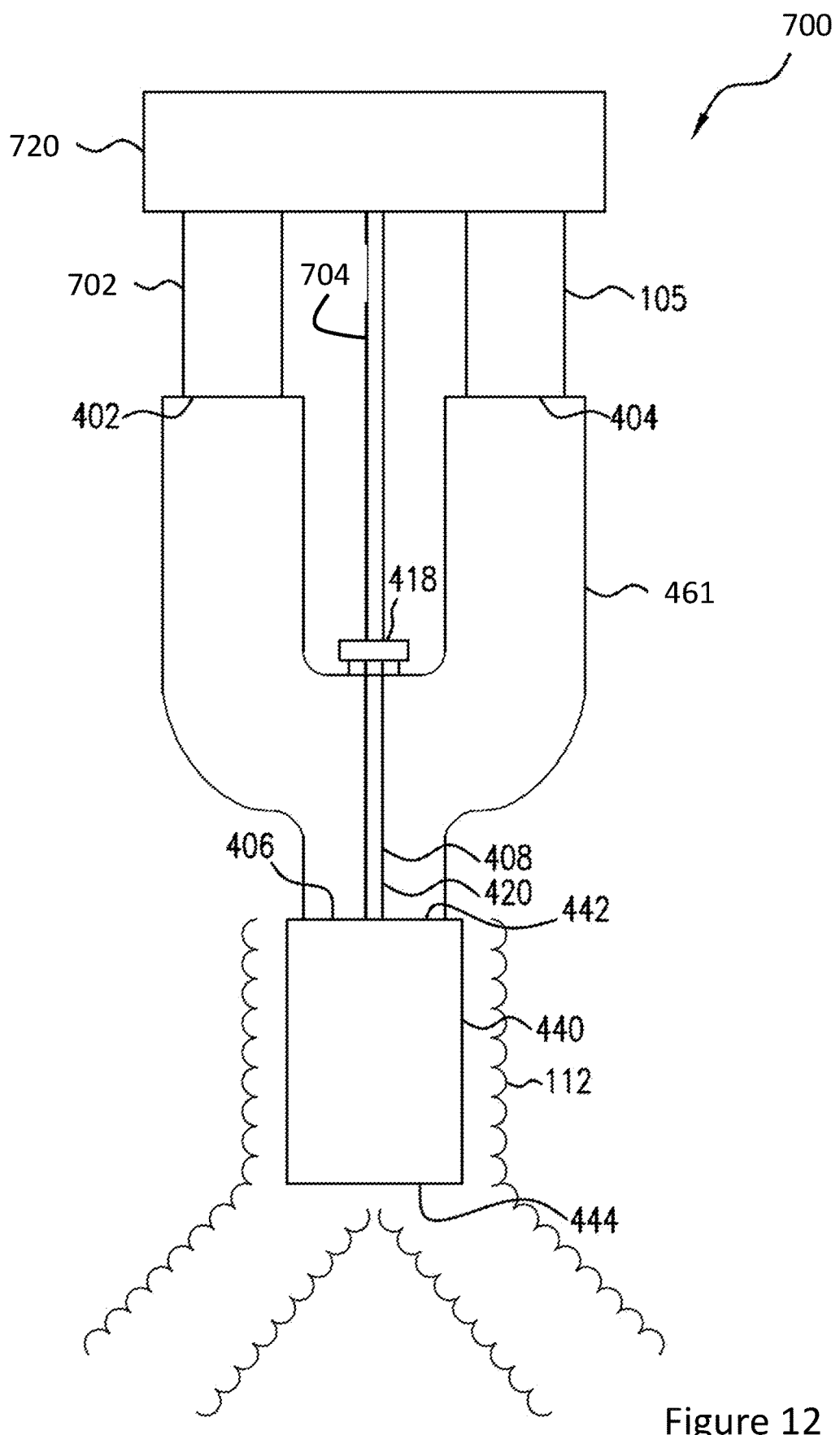
FIG. 12 is a side elevational view of a second variant of the ventilatory assist system of FIG. 8 adapted for operation with the pressure control system of FIG. 11.

FIG. 11 is a block diagram of a pressure control system according to an embodiment. FIG. 12 is a side elevational view of a second variant of the ventilatory assist system of FIG. 8 adapted for operation with the pressure control system of FIG. 11. Considering at once FIGS. 11 and 12, a system 700 for providing ventilatory assist to a patient intubated with an endotracheal tube comprises a manifold, for example the manifold 461 shown on FIG. 9, the manifold 461 being connected to a pressure control system 720 via two (2) inspiratory supply lines 702 and 704 and an expiratory line such as the expiratory line 105 of the previous Figures. The inspiratory supply line 702 is connected to the inspiratory port 402 of the manifold 461. The inspiratory supply line 704 is connected to the inspiratory lumen 408 via the external plug 418. The manifold 461 is connected to the endotracheal tube 440 as illustrated and described in the foregoing description.

The pressure control system 720 is similar to the pressure control system 99 and includes many of the same elements. A pressure feedback system 722 acts as a controller for two (2) inspiratory air sources 724 and 726 that are respectively connected to the inspiratory supply lines 702 and 704. The pressure feedback system 722 controls the inspiratory air source 724 (air source A) to activate an inspiratory flow via the inspiratory supply line 702 toward the inspiratory port 402 of the manifold 461. The pressure feedback system 722 also controls the inspiratory air source 726 (air source B) to produce another inspiratory flow via the inspiratory supply line 704 toward the inspiratory lumen 408. At any given time, the pressure feedback system 722 may activate one or the other or both of the inspiratory flows. It may be observed that, by controlling both inspiratory air sources 724 and 726, the pressure feedback system 722 provides an equivalent function as when the pressure feedback system 300 controls the inspiratory air source 100 and the valve 410 by directing one fraction of the inspiratory flow directly into the endotracheal tube and another fraction of the inspiratory flow via the inspiratory lumen 408.

Though not shown on FIG. 11 for ease of illustration, the pressure control system 720 may also comprise one or more of the gas mixer 350, the hygrometer 352, the humidifier 354, and the oxygen source 356 illustrated on FIG. 3, the gas mixer 350, if present, being connected to one or both of the inspiratory supply lines 702 and 704.

Figure 13:
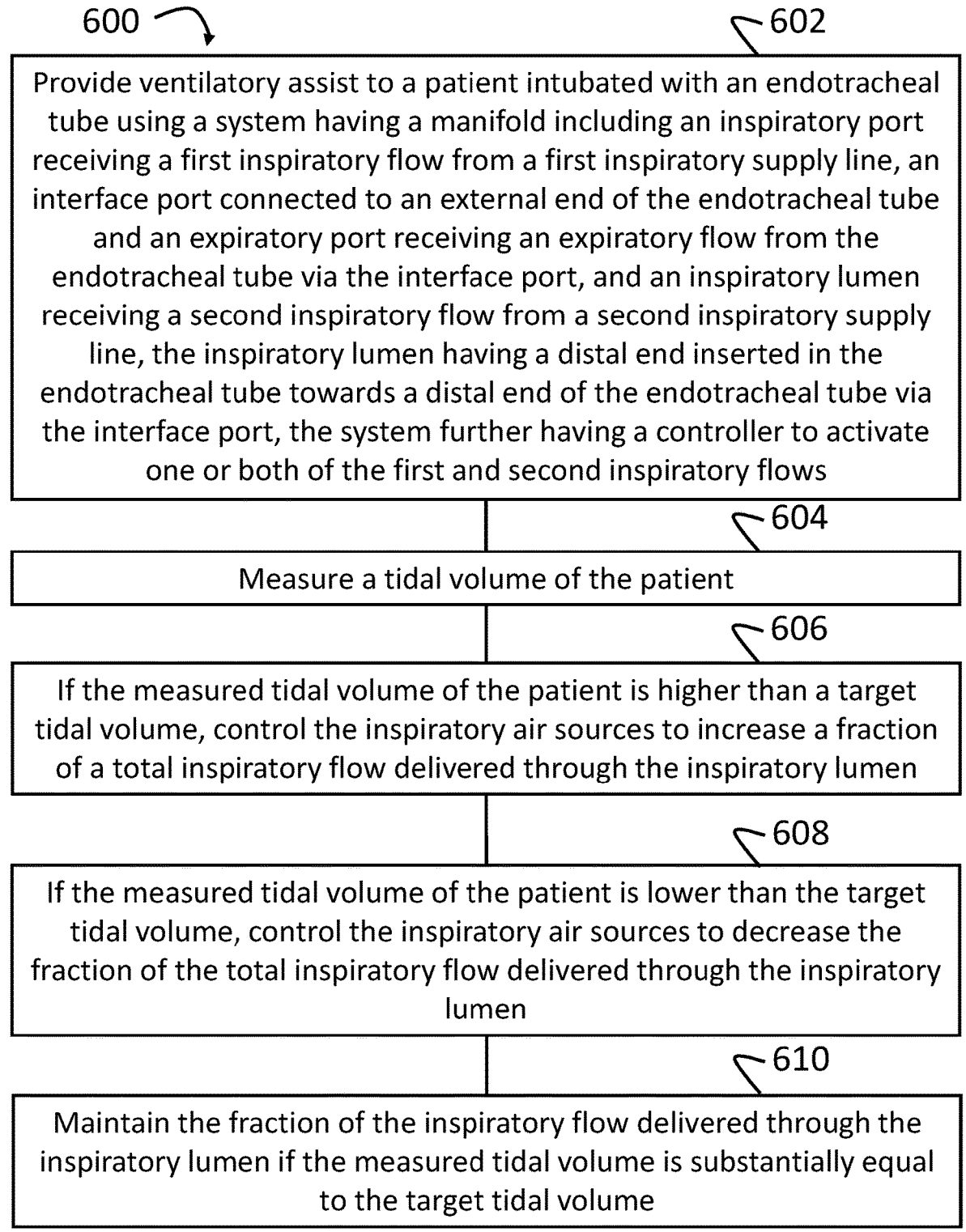
FIG. 13 is a flow chart showing operations of a method of using the ventilatory assist system of FIG. 12.

FIG. 13 is a flow chart showing operations of a method of using the ventilatory assist system of FIG. 12. The flow chart includes a sequence 600 comprising a plurality of operations that may be executed once or repeatedly, at regular intervals or as needed, in variable order, some of the operations possibly being executed concurrently, some of the operations being optional.

Operation 602 of FIG. 13 comprises providing ventilatory assist to an intubated patient using the system of FIGS. 11 and 12. Inspiratory flows provided by the inspiratory air sources 724 and 726 form a total inspiratory flow.

A tidal volume of the patient is measured at operation 604, for example being determined during conventional inspiratory-synchronized assist delivery by a pneumotachograph situated at the level of the endotracheal tube 440. Alternatively, measuring and integrating the total inspiratory flow and the expiratory flow to deduce the tidal volume is also contemplated.

Verification is made at operation 606 to determine if the measured tidal volume of the patient is higher than a target tidal volume, in which case the inspiratory air sources 724 and 726 are controlled by the pressure feedback system 722 to increase a fraction of the total inspiratory flow delivered through the inspiratory lumen 408. At the same time, a remainder of the total inspiratory flow, if any, then flows through the manifold 461, the interface port 406, and the endotracheal tube 440.

At operation 608, if the measured tidal volume of the patient is lower than the target tidal volume, the inspiratory air sources 724 and 726 are controlled by the feedback system 722 to decrease the fraction of the total inspiratory flow delivered through the inspiratory lumen 408 while increasing the remainder of the total inspiratory flow through the manifold 461, the interface port 406, and the endotracheal tube 440.

If the measured tidal volume is substantially equal to the target tidal volume, the fraction of the total inspiratory flow delivered through the inspiratory lumen 408 is maintained at operation 610.

A practitioner may use either methods of FIG. 10 or 13 to bring the same or equivalent benefits to a patient.

Those of ordinary skill in the art will realize that the description of the device, method and system for providing ventilatory assist to a patient are illustrative only and are not intended to be in any way limiting. Other embodiments will readily suggest themselves to such persons with ordinary skill in the art having the benefit of the present disclosure. Furthermore, the disclosed device, method and system may be customized to offer valuable solutions to existing needs and problems related to ventilatory assist to patients.

In the interest of clarity, not all of the routine features of the implementations of device, method and system are shown and described. It will, of course, be appreciated that in the development of any such actual implementation of the device, method and system, numerous implementation-specific decisions may need to be made in order to achieve the developer's specific goals, such as compliance with application-, system- and business-related constraints, and that these specific goals will vary from one implementation to another and from one developer to another. Moreover, it will be appreciated that a development effort might be complex and time-consuming, but would nevertheless be a routine undertaking of engineering for those of ordinary skill in the field of ventilatory assist systems having the benefit of the present disclosure.

In accordance with the present disclosure, the components, process operations, and/or data structures described herein may be implemented using various types of operating systems, computing platforms, network devices, computer programs, and/or general purpose machines. In addition, those of ordinary skill in the art will recognize that devices of a less general purpose nature, such as hardwired devices, field programmable gate arrays (FPGAs), application specific integrated circuits (ASICs), or the like, may also be used. Where a method comprising a series of operations is implemented by a computer or a machine and those operations may be stored as a series of instructions readable by the machine, they may be stored on a tangible medium.

Systems and modules described herein may comprise software, firmware, hardware, or any combination(s) of software, firmware, or hardware suitable for the purposes described herein. Software and other modules may reside on servers, workstations, personal computers, computerized tablets, personal digital assistants (PDA), and other devices suitable for the purposes described herein. Software and other modules may be accessible via local memory, via a network, via a browser or other application or via other means suitable for the purposes described herein. Data structures described herein may comprise computer files, variables, programming arrays, programming structures, or any electronic information storage schemes or methods, or any combinations thereof, suitable for the purposes described herein.

Although the present disclosure has been described hereinabove by way of non-restrictive, illustrative embodiments thereof, these embodiments may be modified at will within the scope of the appended claims without departing from the spirit and nature of the present disclosure.

What is claimed is:

1. A device for providing ventilatory assist to a patient, comprising:
   a manifold including:
      an inspiratory port configured to receive an inspiratory flow from an inspiratory supply line;
      an interface port connectable to an external end of an endotracheal tube; and
      an expiratory port configured to receive an expiratory flow from the endotracheal tube via the interface port;
   an inspiratory lumen having a distal end insertable via the interface port in the endotracheal tube so that the distal end of the inspiratory lumen extends in the endotracheal tube beyond the interface port, a cross-section of the inspiratory lumen being smaller than a cross-section of the endotracheal tube; and
   a multi-position, unitary valve configurable to direct variable fractions of the inspiratory flow from the inspiratory supply line, wherein:
      an entirety of the inspiratory flow is directed to the inspiratory lumen when the valve is in a first configuration,
      the entirety of the inspiratory flow is directed to the endotracheal tube through the interface port without flowing through the inspiratory lumen when the valve is in a second configuration, and
      a fraction of the inspiratory flow is directed to the inspiratory lumen and a remainder of the inspiratory flow being concurrently directed to the endotracheal tube through the interface port when the valve is in a third configuration; and
      wherein the inspiratory lumen does not carry any part of the expiratory flow.

2. The device of claim 1, wherein the inspiratory lumen comprises distal projections configured to maintain the distal end of the inspiratory lumen substantially centered within the cross-section of the endotracheal tube.

3. The device of claim 2, wherein the distal projections comprise a plurality of radial wings protruding from a main tube of the inspiratory lumen, the radial wings being sized to substantially abut an internal wall of the endotracheal tube without impeding the inspiratory flow or the expiratory flow in the endotracheal tube.

4. The device of claim 2, comprising a plurality of sets of distal projections along a length of the distal end of the inspiratory lumen.

5. The device of claim 1, wherein the manifold comprises a sealable port configured for insertion of the distal end of the inspiratory lumen.

6. The device of claim 5, wherein the inspiratory lumen comprises an external plug between a proximal end of the inspiratory lumen and the distal end thereof, the plug being configured to lock in the sealable port.

7. The device of claim 6, wherein the valve is configured to direct at least in part the inspiratory flow to a valve outlet and wherein the proximal end of the inspiratory lumen is configured to connect to the valve outlet.

8. The device of claim 7, wherein the proximal end of the inspiratory lumen is provided with a length that can be cut to adjust to a position of the valve outlet when the plug is locked in the sealable port.

9. The device of claim 1, wherein the valve is configured to modulate a pressure of the inspiratory flow in response to a physiological signal selected from an electrical activation of a diaphragm of the patient (EAdi) and an electromyogram (EMG) signal, the physiological signal being indicative of an inspiratory effort of the patient.

10. The device of claim 1, wherein the valve is configured to synchronize the inspiratory flow to a physiological signal selected from an electrical activation of a diaphragm of the patient (EAdi) and an electromyogram (EMG) signal, the physiological signal being indicative of an inspiratory effort of the patient.

11. The device of claim 1, wherein the valve is configured to adapt the inspiratory flow as a function of respective resistances of the inspiratory lumen and of the endotracheal tube.

12. The device of claim 1, wherein the valve is positioned within the manifold, downstream of the inspiratory port.

13. A method of operating the device of claim 1 to reduce a ventilatory circuit dead space and an anatomical dead space, the method comprising the steps of:
   providing the inspiratory flow from the inspiratory supply line to the inspiratory port of the manifold; and
   operating the valve to direct the entirety of the inspiratory flow from the inspiratory supply line to the inspiratory lumen, or to direct the entirety of the inspiratory flow to the endotracheal tube through the interface port without flowing through the inspiratory lumen, or to concurrently direct the fraction of the inspiratory flow to the inspiratory lumen and the remainder of the inspiratory flow to the endotracheal tube through the interface port.

14. A system for providing ventilatory assist to a patient intubated with an endotracheal tube, comprising:
   the device of claim 1; and
   a first controller configured to control the valve to direct the entirety of the inspiratory flow from the inspiratory port to the inspiratory lumen, or to direct the entirety of the inspiratory flow to the endotracheal tube through the interface port without flowing through the inspiratory lumen, or to concurrently direct the fraction of the inspiratory flow to the inspiratory lumen and the remainder of the inspiratory flow to the endotracheal tube through the interface port.

15. The system of claim 14, further comprising a mechanical ventilator, wherein the valve is positioned on the inspiratory supply line, (a) between the inspiratory port and the mechanical ventilator or (b) in the mechanical ventilator.

16. The system of claim 14, wherein the first controller comprises a pressure feedback system configured to cause the valve to modulate a pressure of the inspiratory flow according to a physiological signal indicative of an inspiratory effort of the patient.

17. The system of claim 16, wherein the pressure feedback system is responsive to at least one measurement selected from an electrical activation of the patient's diaphragm (EAdi), an electromyogram (EMG) signal, the pressure of the inspiratory flow, an expiratory flow, the inspiratory flow, an inspiratory pressure, an end tidal carbon dioxide value, an arterial carbon dioxide pressure, and a combination thereof.

18. The system of claim 16, comprising:
   a second controller of an expiratory port pressure, responsive to the physiological breathing signal indicative of the patient's inspiratory effort and configured to allow an unrestricted air flow through the expiratory port during the patient's expiration phase and to partially restrict the air flow through the expiratory port to a minimum air flow during the patient's inspiration phase;

whereby, during both the patient's inspiration and expiration phases, a unidirectional air flow is produced through the inspiratory lumen and the expiratory port to prevent air expired by the patient from being breathed again.

19. The system of claim 14, comprising a pressure feedback system connected to the first controller and configured to cause the valve to synchronize the inspiratory flow with a physiological signal indicative of an inspiratory effort of the patient.

20. A method of operating the system of claim 14, to reduce a ventilatory circuit dead space and an anatomical dead space, the method comprising the steps of:
providing the inspiratory flow from the inspiratory supply line to the inspiratory port of the manifold; and
operating the valve to direct the entirety of the inspiratory flow from the inspiratory supply line to the inspiratory lumen, or to direct the entirety of the inspiratory flow to the endotracheal tube through the interface port without flowing through the inspiratory lumen, or to concurrently direct the fraction of the inspiratory flow to the inspiratory lumen and the remainder of the inspiratory flow to the endotracheal tube through the interface port.

21. A method of providing ventilatory assist to a patient intubated with an endotracheal tube, comprising:
providing ventilatory assist to the patient using the system of claim 15;
measuring a tidal volume of the patient;
if the measured tidal volume of the patient is higher than a target tidal volume, increasing the fraction of the inspiratory flow delivered through the inspiratory lumen; and
if the measured tidal volume of the patient is lower than the target tidal volume, decreasing the fraction of the inspiratory flow delivered through the inspiratory lumen.

22. The method of claim 21, comprising maintaining the fraction of the inspiratory flow delivered through the inspiratory lumen if the measured tidal volume is substantially equal to the target tidal volume.

23. The method of claim 21, wherein the method reduces a ventilatory circuit dead space and an anatomical dead space.

24. A method of providing ventilatory assist to a patient intubated with an endotracheal tube, comprising:
providing ventilatory assist to the patient using the system of claim 16;
measuring a tidal volume of the patient;
if the measured tidal volume of the patient is higher than a target tidal volume, increasing the fraction of the inspiratory flow delivered through the inspiratory lumen; and
if the measured tidal volume of the patient is lower than the target tidal volume, decreasing the fraction of the inspiratory flow delivered through the inspiratory lumen; wherein increasing or decreasing the fraction of the inspiratory flow delivered through the inspiratory lumen is performed in synchrony with the physiological signal indicative of the inspiratory effort of the patient.

25. The method of claim 24, comprising maintaining the fraction of the inspiratory flow delivered through the inspiratory lumen if the measured tidal volume is substantially equal to the target tidal volume.

26. The method of claim 24, wherein the method reduces ventilatory circuit dead space and anatomical dead space.

27. A system for providing ventilatory assist to a patient, comprising:
a manifold including:
an inspiratory port configured to receive a first inspiratory flow from a first inspiratory supply line;
an interface port connectable to an external end of an endotracheal tube and allowing the first inspiratory flow to be delivered to airways of the patient through the endotracheal tube; and
an expiratory port configured to receive an expiratory flow from the endotracheal tube via the interface port; and
an inspiratory lumen configured to receive a second inspiratory flow from a second inspiratory supply line, the inspiratory lumen having a distal end insertable via the interface port in the endotracheal tube so that the distal end of the inspiratory lumen extends in the endotracheal tube beyond the interface port, the distal end of the inspiratory lumen being insertable toward a distal end of the endotracheal tube, allowing the second inspiratory flow to be delivered to the airways of the patient, the second inspiratory flow being separated from the first inspiratory flow along an inserted length of the inspiratory lumen within the endotracheal tube, a cross-section of the inspiratory lumen being smaller than a cross-section of the endotracheal tube; and
a pressure control system responsive to a physiological signal selected from an electrical activation of a diaphragm of the patient (EAdi) and an electromyogram (EMG) signal to selectably direct only the first inspiratory flow to the inspiratory port of the manifold, only the second inspiratory flow to the inspiratory lumen, or at once the first inspiratory flow to the inspiratory port of the manifold and the second inspiratory flow to the inspiratory lumen.

28. The system of claim 27, comprising:
a first inspiratory air source controlled by the pressure control system and connected to the first inspiratory supply line to produce the first inspiratory flow; and
a second inspiratory air source controlled by the pressure control system and connected to the second inspiratory supply line to produce the second inspiratory flow.

29. A method of providing ventilatory assist to a patient intubated with an endotracheal tube, the method comprising:
providing ventilatory assist to the patient using the system of claim 27, wherein the second inspiratory flow is a fraction of a total inspiratory flow including the first and second inspiratory flows;
measuring a tidal volume of the patient;
if the measured tidal volume of the patient is higher than a target tidal volume, increasing the fraction of the total inspiratory flow delivered through the inspiratory lumen; and
if the measured tidal volume of the patient is lower than the target tidal volume, decreasing the fraction of the total inspiratory flow delivered through the inspiratory lumen.

30. The method of claim 29, wherein the method reduces a ventilatory circuit dead space and an anatomical dead space.

31. A manifold adapted for connection to a device for providing ventilator assist to a patient, said manifold including:
an inspiratory port connectable to an inspiratory supply line;

an expiratory port configured to receive an expiratory flow from the endotracheal tube via an interface port;

a sealable port configured for insertion of an inspiratory lumen so that the distal end of the inspiratory lumen extends in the endotracheal tube beyond the interface port;

the interface port connectable to an external end of an endotracheal tube;

the expiratory port configured to receive an entirety of the expiratory flow from the endotracheal tube via the interface port so that the inspiratory lumen does not carry any part of the expiratory flow; and a multi-position, unitary valve configurable to direct variable fractions of an inspiratory flow from the inspiratory port, wherein:

an entirety of the inspiratory flow is directed to the inspiratory lumen when the valve is in a first configuration, the entirety of the inspiratory flow is directed to the endotracheal tube through the interface port without flowing through the inspiratory lumen when the valve is in a second configuration, and a fraction of the inspiratory flow is directed to the inspiratory lumen and a remainder of the inspiratory flow being concurrently directed to the endotracheal tube through the interface port when the valve is in a third configuration.

\* \* \* \* \*